US005275153A

United States Patent [19]

Kay

[11] Patent Number: 5,275,153

[45] Date of Patent: Jan. 4, 1994

[54] DEMAND VALVE HAVING REACTION LOAD MEANS AND AN INSERTABLE TRIGGER ELEMENT

[75] Inventor: Francis X. Kay, Akeley, England

[73] Assignee: F.X.K. Patents Limited, Akeley, England

[21] Appl. No.: 675,288

[22] Filed: Mar. 26, 1991

[30] Foreign Application Priority Data

Mar. 29, 1990 [GB] United Kingdom ................. 9007020

[51] Int. Cl.[5] ........................ A62B 9/02; A62B 18/10; A61M 16/00; G05D 7/00

[52] U.S. Cl. .......................... 128/205.24; 128/201.28; 128/204.26; 137/102

[58] Field of Search ...................... 128/201.28, 205.24, 128/204.26; 251/90, 93; 137/102, 494, 495, 907

[56] References Cited

U.S. PATENT DOCUMENTS

| | | | |
|---|---|---|---|
| 3,047,001 | 7/1962 | Hosford | 128/204.26 |
| 3,524,464 | 8/1970 | Glidden . | |
| 4,082,093 | 4/1978 | Fry et al. | 128/204.26 |
| 4,147,176 | 4/1979 | Christianson | 128/204.26 |
| 4,159,717 | 7/1979 | Cossey | 128/204.26 |

FOREIGN PATENT DOCUMENTS

| | | | |
|---|---|---|---|
| 1104829 | 4/1961 | Fed. Rep. of Germany . | |
| 719025 | 11/1954 | United Kingdom | 128/204.26 |
| 938649 | 10/1963 | United Kingdom . | |
| 1224478 | 3/1971 | United Kingdom | 128/204.26 |
| 1432171 | 4/1976 | United Kingdom | 123/205.24 |
| 1511844 | 5/1978 | United Kingdom | 128/204.26 |
| 2143137 | 6/1985 | United Kingdom . | |

*Primary Examiner*—Edgar S. Burr
*Assistant Examiner*—Kimberly L. Asher
*Attorney, Agent, or Firm*—Vaden, Eickenroht, Thompson, Boulware & Feather

[57] ABSTRACT

Emergency breathing equipment intended to provide short term life support by ducting breathable gas from a small capacity source to a user via a restricted flow path that allows only limited flow rates so as to prevent hyperventilation and wastage of breathable gas is characterised by a demand valve having the poppet controlled by a demand pressure-sensing diaphragm to control an inhalation flow path, the diaphragm also controlling an exhalation flow path so as to switch the user between said flow paths by opening one and closing the other, as it moves between two positions under the influence of demand pressure. The equipment is also characterised by a reactive pressure regulator for the breathable gas and having its delivery pressure switchable by a trigger element that in an installed position unloads the reaction member so as to provide zero delivery pressure, withdrawal of the trigger element allowing the reaction load to operate to set a fixed positive delivery pressure.

10 Claims, 2 Drawing Sheets

Fig.1.
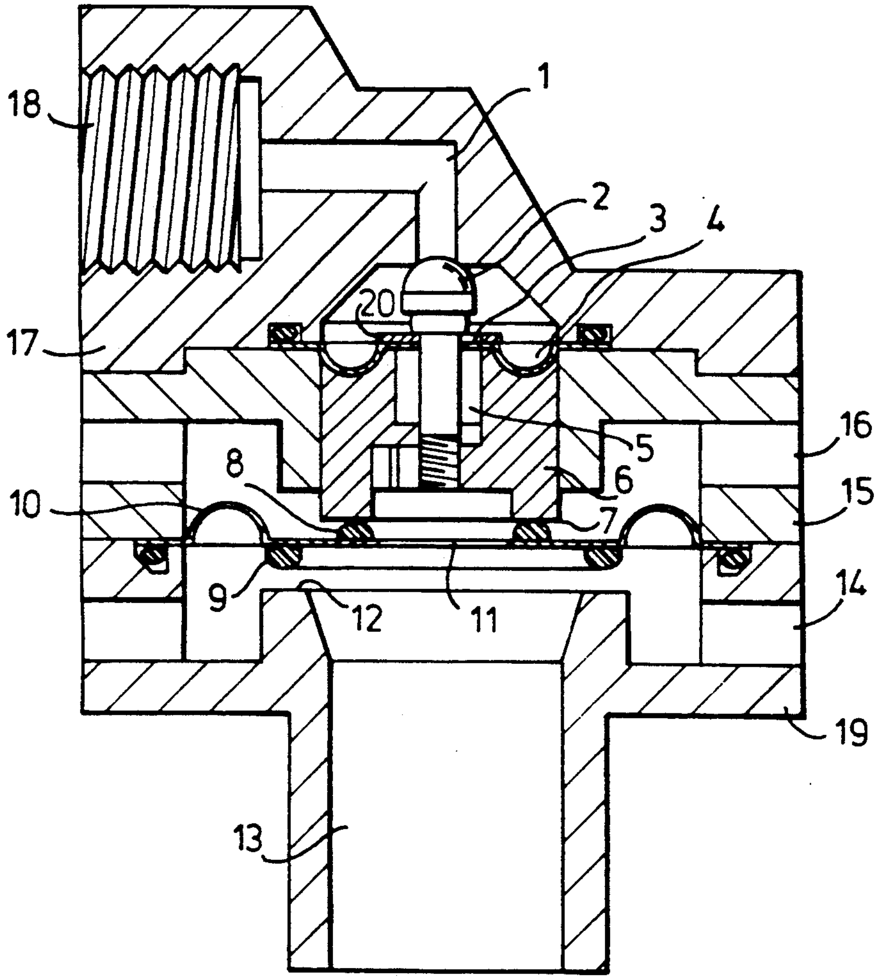
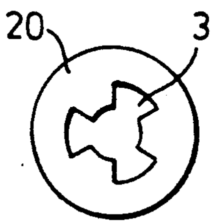
Fig.2.

DEMAND VALVE HAVING REACTION LOAD MEANS AND AN INSERTABLE TRIGGER ELEMENT

TECHNICAL FIELD

The invention relates to emergency breathing equipment intended to provide a short term supply of breathable gas to a user in a hazardous atmosphere or during temporary submersion. Applications of the equipment to which the invention is directed are escape from smoke-filled enclosures such as aircraft cabins by aircrew and passengers or from military vehicles or vessels; crew escape from submerged enclosures such as ditched aircraft and helicopters; and immediate use by rescue personnel such as firefighters, ambulance crews and so on in the absence of or while donning conventional long term self contained breathing equipment.

BACKGROUND

For the applications envisaged it is important that the equipment should be compact and light in weight; be rugged and simple to use, especially by unpractised users; and be reliable and self-adapting to the requirements of different users and different operational circumstances.

Breathing equipment for these purposes essentially comprises a suitable self-contained source of breathable gas such as clean air stored at high pressure in a suitable vessel; and means for delivering this breathing gas at a suitable pressure and in required quantities to a point of use such as a breathing mask: that is to say, the essential components correspond with those of a conventional, self-contained breathing apparatus, the means : for delivery of breathing gas at a required pressure and in required quantities typically comprising a pressure-regulator and suitable flow-control devices that may include a demand valve. However, whereas conventional self-contained breathing apparatus is typically intended for use by trained users practised in its use and capable, therefore, of using provided adjusting means to regulate gas delivery, the equipment to which the invention is directed needs to be self-regulating and self-adapting without the necessity of making any adjustments. Ideally, moreover, it should operate to mitigate the potential dangers to a user arising from misuse, e.g. due to inexperience.

The different lung capacities of individuals affect the rate of air consumption at maximum breathing rates such as occur when the individual is engaged in strenuous physical activity or is subjected to high general stress levels. However the air consumption rate necessary to sustain life is in general substantially less than the maximum corresponding with unrestrained breathing and in many circumstances a restraint on breathing rate is desirable to prevent hyperventilation and its undesirable physiological consequences. Indeed, if there is restraint upon the rate of air consumption not only is hyperventilation prevented but a calming influence is exerted. Accordingly while the lung capacities of individuals may differ significantly, their air consumption rates at a life-sustaining level are remarkably similar. The present invention utilises this phenomenon.

SUMMARY OF THE INVENTION

In one aspect, the invention provides emergency breathing equipment that is characterised by a demand valve comprising a poppet controlling a restricted inhalation flow path from a breathing gas inlet to a user connection, said poppet being operable by a demand pressure-sensing diaphragm exposed to said user connection and also controlling an exhalation flow path between the user connection and an exhaust port such that demand pressure changes shift the diaphragm between a first position in which the poppet opens the inhalation flow path and the diaphragm closes the exhalation flow path, and a second position in which the poppet closes the inhalation flow path and the diaphragm opens the exhalation flow path.

In preferred embodiments, the diaphragm actuates the poppet through a pusher member partly defining the inhalation flow path and itself subject to demand pressure independently of the diaphragm to provide for secondary control of the poppet in the event of failure of the diaphragm, movement of the pusher member relative to the diaphragm both operating the poppet and controlling an auxiliary exhalation flow path.

The construction of the demand valve permits the gas spaces therewithin to be of small volume, thereby providing for sensitivity and rapid response to demand pressure changes, while avoiding wastage of breathing gas during valve changeover in a breathing cycle. The construction further permits the demand valve to have small overall physical size such as to make its integration in a simple lightweight breathing mask a practical possibility.

The invention also consists in emergency breathing equipment that is characterised by a reactive pressure regulator (such as for instance disclosed in GB-A-1 511 844) adapted to deliver breathing gas at a fixed low pressure from a high pressure source, but modified in accordance with this invention by having its reaction load means controlled by a removable or displaceable trigger element that in an installed position disables the reaction load means, to permit the inlet valve means of the regulator to remain closed.

Because the regulated output pressure of a reactive pressure regulator is a function of the load to which its reaction member is exposed, disablement of the reaction load means (to prevent these applying load to the reaction member) zeroes the output pressure. Accordingly, the trigger element serves to switch the regulator output pressure between zero and the fixed low pressure setting for breathing gas delivery, thereby providing efficient on/off switching of the regulator output.

The trigger element is preferably operable by another part of the equipment in such manner that the regulator is automatically switched to deliver breathing gas by the act of moving that other part of the equipment from a stowed out of use condition. In preferred embodiments, the trigger element forms part of a breathing mask or demand valve. The trigger element may for instance take the form of a probe that, inserted into a passage in the regulator body, operates a follower mechanism interposed between the reaction load means and the reaction member to withdraw the former from the latter. The probe may be formed with a detent notch to receive a detent when fully inserted, thereby to retain the probe in position and to avoid its inadvertent withdrawal.

THE DRAWINGS

A preferred embodiment of the invention is described below, with reference to the accompanying drawings, in which:

FIG. 1 is an axial section of a preferred form of demand valve;

FIG. 2 is a fragmentary plan of a backing plate component of the demand valve of FIG. 1.

DESCRIPTION OF PREFERRED EMBODIMENTS

Figure 3:
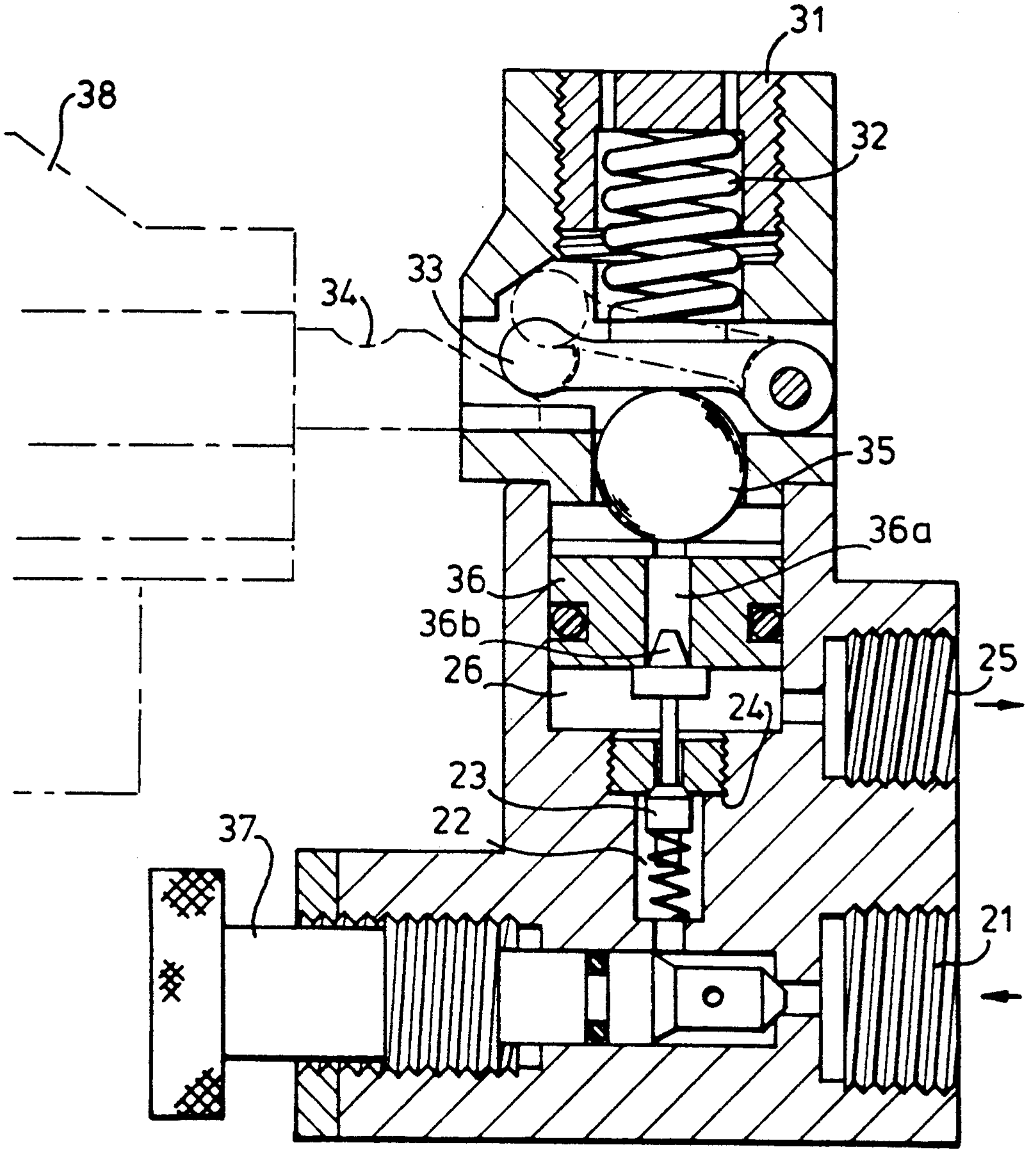
FIG. 3 is an axial section of a reactive pressure regulator.

The demand valve illustrated in FIGS. 1 and 2 comprises a body having a control inlet passage 1 terminating in a seat for a poppet 2 that has a stem extending through a sealing diaphragm 4 and into a central passageway 5 in a pusher member 6 axially movable in the body. The distal end of the poppet stem is stepped to engage a step in the pusher member 6 for transmission of thrust. The end of the pusher member remote from inlet passage 1 is formed with a central recess connected with the passageway 5, bounded by a seat 7 for a seal 8 on the inner periphery of an annular demand pressure-sensing diaphragm 10 having on its opposite face a seal 9 and a central aperture 11 The seal 9 is positioned, outboard of seal 8, for cooperation with a seat 12 surrounding an axial user connection port 13 in the body. The body is constructed of a centre section 15 comprising exhaust ports 14 and 16; an upper cap 17 in which the inlet passage 1 is formed and provided with an inlet connection port 18; and a lower cap 19 formed with a spigot providing the user connection port 13.

The diaphragm 4 provides a low friction seal between the pusher member 6 and the centre section 15 of the body. The centre of diaphragm 4 is fitted with a backing plate 20 lodged on a step on the stem of poppet 2 and formed with slots 3 to provide a flow path through the diaphragm: that is, the inlet passage 1, slots 3, passageway 5 and aperture together constitute an inhalation flow path for breathing gas, controlled by poppet 2, from the inlet port 18 to the user connection port 13.

The seal 9 controls a normal exhalation flow path between the port 13 and the exhaust ports 14, while the seal 8 controls an auxiliary flow path between the inlet flow path, and the port 13, and the exhaust ports 16.

In operation of this demand valve, and assuming a source of breathing gas at suitable pressure connected to port 18, an attempt by the user to inhale through port 13 causes downwards movement of the diaphragm 10 and, with it, the pusher member 6, diaphragm 4 and poppet 2, to open the inhalation flow path while closing the exhalation flow path.

Exhalation, on the other hand, raises the diaphragm 10 to close the inhalation flow path while opening the (normal) exhalation flow path to the ports 14. However, should the diaphragm 10 stick, the exhalation pressure will act on the pusher member 6 to cause this to move upwardly independently of the diaphragm 10 and so unseat the seal 8 from seat 7 and open the auxiliary flow path to the ports 16. Moreover, should the poppet 2 be forced open by excess pressure in the passage 1—for instance caused by regulator malfunction—the auxiliary flow path will also open to provide relief flow to the ports 16.

It will be seen that the construction is very compact and that the volume of the inhalation flow path is very small so that breathing gas wastage is minimised. Moreover the construction provides safeguards against malfunction.

FIG. 3 illustrates a preferred form of reactive pressure regulator for breathing equipment embodying the invention. The general construction of this regulator is as disclosed in GB-A-1 511 844. It comprises a body having an inlet port 21 adapted for connection to a high pressure breathing gas source such as a 0.25 liter bottle charged with clean air at 207 ats. (providing about 2 liters of air at normal pressure). The inlet port 21 is connected to a valve chamber 22 housing a spring-loaded poppet 23 engaging a seat 24 surrounding a passage to an outlet port 25 in a reaction chamber 26. A reaction member 36 has an axial overpressure relief passage **36*a* normally sealed by a valve member 36*b* on the upper end of the poppet 23 and is exposed to pressure in chamber 26 and to a reaction load applied by a spring 32 and ball 35 and adjusted by screwcap 31. As is known, the pressure at outlet port 25 is determined by the load on reaction member 36 that at the set pressure allows the poppet 23 to close. Overpressure at the outlet port 25 and in the chamber 26 lifts the reaction member 36 away from the valve member 36*b* to provide relief via the passage 36*a***.

In accordance with the invention, the basic construction is modified, as shown, to provide for unloading of the reaction member 36 by insertion into the valve body of a trigger element in the form of a probe 34 to engage a follower 33 interposed between the spring 32 and the ball 35, so as to withdraw the spring load from the latter and thereby allow the poppet 23 to close under its own spring load. As shown, the probe 34 is ramped to accomplish displacement of the follower 33 on insertion, and has a detent notch to retain the probe in its fully inserted position, against inadvertent withdrawal. The probe 34 is conveniently provided on a face mask 38 as shown in outline, to provide for stowage of the latter and to ensure automatic withdrawal of the probe (to set the regulator to deliver breathing gas) by the act of removing the face mask from stowage for use. Moreover, such automatic switching of the regulator will ensure purging of the mask before its donning, particularly important if donning takes place while submerged.

As shown the regulator has a screwdown valve 37 to close the inlet during long term storage of the equipment. The valve 37 may be fitted internally with a pressure relief valve to control charging of the air storage bottle with the regulator in situ or to guard against the dangers of excessive stored air pressure rise in the storage bottle.

In breathing equipment according to the invention, the inlet port 18 of the demand valve of FIGS. 1 and 2 would be connected to the regulated pressure outlet port 25 of the pressure regulator of FIG. 3 by a suitable flexible hose such as a nylon pipe of about 4 mm OD.

Equipment according to the invention may provide for several minutes breathing at a life support rate and yet be of such a size and weight as to allow its being stowed in a small pack suitable for attachment to an airman's flying suit or to a lifejacket, or to an aircraft seat.

I claim:

1. Emergency breathing equipment comprising a demand valve, said demand valve having a breathing gas inlet, a user connection having a seat thereabout and an inhalation flow path extending from said inlet to said user connection; a fixed restriction in said inhalation flow path to limit breathing gas flow therethrough; an exhaust port and an exhalation flow path extending from said user connection to said exhaust port; a poppet controlling flow in said inhalation flow path; a demand pressure-sensing diaphragm having a seal surface on one side and exposed to said user connection and operatively connected to said poppet to open the inhalation flow path in response to user demand; said diaphragm being movably between a first position in which the poppet opens the inhalation flow path and the seal surface seals on the seat about the user connector to close the exhalation flow path, and a second position in which the poppet closes the inhalation flow path and the seal surface disengages the seat to open the exhalation flow path, said demand valve breathing gas inlet being connected to a reactive pressure regulator adapted to deliver thereto breathing gas at a fixed low pressure from a high pressure source and having an inlet and outlet connected by a passageway, valve means normally urged to a position closing the passageway intermediate the inlet and outlet, a reaction member in the passageway responsive to outlet pressure, reaction load means urging the reaction member toward a position to open the valve means, and a trigger element insertable between the load means and reaction member to disable the load means and thereby permit the valve means to remain closed.

2. Emergency breathing equipment comprising a reactive pressure regulator delivering breathing gas at a fixed low pressure from a high pressure source and having an inlet and outlet connected by a passageway, valve means normally urged to a position closing the passageway intermediate the inlet and outlet, a reaction member in the passageway responsive to outlet pressure, reaction load means urging the reaction member toward a position to open the valve means, and a trigger element insertable between the load means and reaction member to disable the load means and thereby permit the valve means to remain closed.

3. The equipment of claim 2 or 1, wherein said equipment includes another part having a stowed position relative to the regulator and connected to said trigger element, said trigger element being movable out of said disabling position in response to movement of said another part of the equipment from said stowed position.

4. The equipment of claim 2 or 1, wherein said trigger element is carried by a breathing mask or demand valve.

5. The equipment of claim 2 or 1, wherein said regulator includes a reaction member, and said trigger element comprises a probe inserted into the regulator to operate a follower mechanism interposed between the reaction load means and the reaction member to withdraw the reaction load means from the reaction member.

6. The equipment of claim 5, in which said regulator includes a detent and said probe has a detent notch to receive the detent for holding the trigger element when fully inserted in the regulator.

7. Emergency breathing equipment comprising a demand valve, said demand valve having a breathing gas inlet, a user connection and an inhalation flow path extending from said inlet to said user connection; a restriction in said inhalation flow path to limit breathing gas flow therethrough; main and auxiliary exhaust ports, a main exhalation flow path extending from said user connection to said main exhaust port; a poppet controlling flow in said inhalation flow path; a demand pressure-sensing diaphragm exposed to said user connection; a pusher member partly defining said inhalation flow path and transmitting thrust from said diaphragm to said poppet, an auxiliary exhalation flow path extending from said user connection to said auxiliary exhaust port; said diaphragm being responsive to user demand pressure at said user connection to move between a first position in which it opens said inhalation flow path and closes said exhalation flow paths and a second position in which it closes the inhalation flow path and opens said main exhalation flow path; and said pusher member being responsive to user demand pressure independently of said diaphragm to operate said poppet and to control said auxiliary exhalation flow path.

8. The equipment of claim 7, comprising an auxiliary exhalation valve seat on said pusher member and a valve seal on said diaphragm to cooperate therewith and to transmit thrust from the diaphragm to the pusher member.

9. The emergency breathing equipment of claim 8, having said breathing gas inlet connected to a reactive pressure regulator adapted to deliver thereto breathing gas at a fixed low pressure from a high pressure source and having an inlet and outlet connected by a passageway, valve means normally urged to a position closing the passageway intermediate the inlet and outlet, a reaction member responsive to outlet pressure, reaction load means urging the reaction member toward a position to open the valve means an a trigger element insertable between the load means and reaction member to disable the load means and thereby permit the valve means to remain closed.

10. The equipment of claim 7, having its said demand valve breathing gas inlet connected to a reactive pressure regulator adapted to deliver thereto breathing gas at a fixed low pressure from a high pressure source and having an inlet and outlet connected by a passageway, valve means normally urged to a position closing the passageway intermediate the inlet and outlet, a reaction member in the passageway responsive to outlet pressure, reaction load means urging the reaction member toward a position to open the valve means, and a trigger element insertable between the load means and reaction member to disable the load means and thereby permit the valve means to remain closed.

* * * * *